United States Patent [19]

Fields et al.

[11] Patent Number: 4,526,986
[45] Date of Patent: Jul. 2, 1985

[54] HALOMETHYL, METHYL MALEIC ANHYDRIDE AND SYNTHESIS OF BROMOMETHYL, METHYL MALEIC ANHYDRIDE

[75] Inventors: Ellis K. Fields, River Forest; Mark L. Winzenburg, Naperville, both of Ill.

[73] Assignee: Standard Oil Company (Indiana), Chicago, Ill.

[21] Appl. No.: 484,541

[22] Filed: Apr. 13, 1983

[51] Int. Cl.³ ............................................. C07D 307/60
[52] U.S. Cl. .................................... 549/254; 166/275; 252/8.55 D; 549/253; 204/158 HA
[58] Field of Search ................. 549/254; 204/158 HA

[56] References Cited

PUBLICATIONS

Bennett, Concise Chem. and Tech. Dictionary, (1974), p. 547.
Hawley, The Condensed Chem. Dictionary, 10th Ed., Van Nostrand, (1981), p. 535.
Considine, Chemical and Process Technology Encyclopedia, (1980), McGraw-Hill, p. 578.
McElvain et al., J.A.C.S., vol. 64, pp. 260–265, (1942).
Huyser et al., J.A.C.S., pp. 391–396, (1960), vol. 82.
Laursen et al., J. of Med. Chem., pp. 619–620, vol. 14(7), (1971).
Greenlee et al., Tetrahedron, vol. 36, pp. 3367–3375, (1980).
Boeckman, Jr. et al., J.A.C.S., vol. 102, pp. 7146–7149, (1980).

*Primary Examiner*—Henry R. Jiles
*Assistant Examiner*—Bernard I. Dentz
*Attorney, Agent, or Firm*—William C. Clarke; William T. McClain; William H. Magidson

[57] ABSTRACT

Quaternary ammonium compounds containing anhydride groups are prepared by halogenating dimethylmaleic anhydride and reacting the halogenated product with a tertiary amine. The products are useful as surfactants, biocides and as cosurfactants in enhanced oil recovery.

3 Claims, No Drawings

HALOMETHYL, METHYL MALEIC ANHYDRIDE AND SYNTHESIS OF BROMOMETHYL, METHYL MALEIC ANHYDRIDE

FIELD OF THE INVENTION

This invention relates to quaternary ammonium compounds containing anhydride groups that are derived from dimethylmaleic anhydride. More particularly, this invention relates to quaternary ammonium compounds prepared by halogenating dimethylmaleic anhydride with a halogen, an allylic halogenating agent, or a free radical halogenating agent and reacting the methyl halomethylmaleic anhydride with tertiary amines wherein the said quaternary ammonium compounds are of the structural formula:

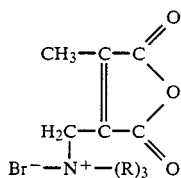

wherein R is selected from the group consisting of alkyl groups of 1 to 20 carbon atoms, aryl groups of 6 to 18 carbon atoms, aralkyl groups with 7 to 19 carbon atoms, heterocyclic groups with 4 to 20 carbon atoms, and cycloalkyl groups with 5 to 12 carbon atoms.

For convenience these compounds are referred to as quaternary ammonium compounds containing anhydride groups. These compounds possess biocidal properties. The invented compounds of molecular weights within the range of from about 400 to about 1200 act as cosurfactants useful in enhanced oil field recovery. These compounds are also useful as surfactants and biocides, and can be used as hydraulic fluids when of sufficiently low molecular weight, and as chemical intermediates.

Cosurfactants function as coupling agents for surfactants and reservoir brines for the purpose of enhancing crude oil production. Surfactant and cosurfactant mixtures are dissolved in brines in low concentrations to form micellar fluids or solutions. These micellar solutions can be described as microemulsions containing surfactants which act to reduce the interfacial tension between water and oil. A second component, a cosurfactant, usually an alcohol, is used to improve the quality of the micellar solution. An efficient cosurfactant increases the micelles' capacity to solubilize more oil or water and still form stabilized solutions.

Compounds used as cosurfactants in the prior art have been alcohols such as isopropyl alcohol, amyl and hexyl alcohols and their ethoxylated derivatives. These cosurfactants have limited capabilities because of the variety of reservoir conditions encountered in enhanced oil recovery programs. For example, special systems must be designed for reservoirs which are essentially fresh water, that is, those which contain 6000 ppm or less monovalent ions, and those which are essentially hard water, those which contain 50,000 ppm monovalent ions plus 500 ppm or more of divalent ions. Cosurfactants should perform so as to achieve a stable fluid when the water-cosurfactant mixture is in contact or mixed with crude oil. Molecular weight of the cosurfactant should be sufficiently low to permit passage through semipermeable rock formations and achieve mobility control.

This invention accordingly relates to a new and unique family of low molecular weight compounds which are suitable for use as cosurfactants for enhanced crude oil recovery. These compounds in use lower the interfacial tension between water and oil, are low molecular weight of from about 400 to about 1200, and are required in only low concentrations to formulate micellar fluids.

SUMMARY OF THE INVENTION

This invention relates to quaternary ammonium compounds containing anhydride groups that are derived from dimethylmaleic anhydride, and that are useful as cosurfactants in enhanced oil recovery, surfactants and biocides, and as hydraulic fluids when of sufficiently low molecular weight.

DETAILS OF THE INVENTION

Quaternary ammonium compounds containing anhydride groups are prepared by halogenating dimethylmaleic anhydride with an allylic halogenating agent and reacting the methyl halomethylmaleic anhydride with tertiary amines according to the following reaction:

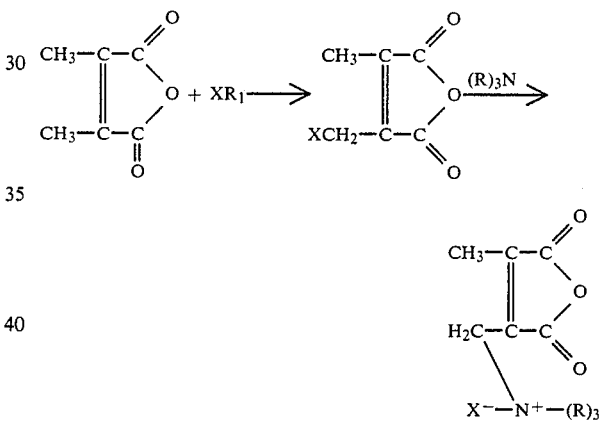

$R_1$ can be halogen, such as chlorine or bromine, succinimido and trichloromethyl. X is halogen and can be iodine, bromine, chlorine and fluorine. Chlorine and bromine are preferred because of availability and cost.

The tertiary amine, $(R)_3N$, can be a trialkyl amine wherein the alkyl group can be of 1 to 20 carbon atoms. Examples of such trialkyl amines are trimethylamine, triethylamine, tributylamine, lauryldimethylamine, stearyldimethylamine and tri-n-octylamine. The tertiary amines can be heterocyclic amines selected from the group consisting of pyridine, quinoline, isoquinoline, phenanthridine and N-methylpyrrolidine. Examples of aralkyl amines are benzyldimethylamine, benzyldibutylamine, and naphthylmethyl dimethylamine.

Preferably the tertiary amine comprises an amine comprising trioctylamine, triethylamine, trihexylamine, stearyldimethylamine and pyridine. These are preferred because they are cheap, reactive and cover the range of derivatives in various inorganic and organic solvents. One or more hydrogens of the aliphatic, alicyclic, heterocyclic and aromatic moieties of the above-described amine compounds can be replaced with nonreactive radical groups such as cyano and alkoxy radicals.

The molar ratios of the reactants to prepare the quaternary ammonium compounds containing anhydride groups, i.e., the allylic halogenating agent, and the anhydride that can be used, can vary. The agent-anhydride ratio is between 1 to 3 moles of agent per mole of anhydride. Substantially equimolar amounts of agent and anhydride are preferred. Use of a solvent such as heptane, hexane, benzene, acetone, dichloromethane, dioxane or carbon tetrachloride at concentrations of 1 to 85 weight percent is convenient.

Dichloromethane is the preferred solvent.

The reaction can be run in any type of open or sealed vessel, suitably agitated, equipped with means of heating the contents and with reflux capabilities.

The present invention also comprises a method of injecting a miceller slug into a subterranean formation comprising the steps of (1) contacting said subterranean formation with an aqueous fluid composition comprising water, a surfactant, a hydrocarbon, and an electrolyte and a low molecular weight quaternary ammonium compound containing anhydride groups within the range of from about 400 to about 1200; (2) applying sufficient pressure to said composition to cause said micellar slug to move through said formation; (3) maintaining sufficient pressure while injecting said composition into said formation. The said low molecular weight quaternary ammonium compounds can be selected from the group consisting of compounds prepared from trioctylamine, trihexylamine and stearyldimethylamine.

In order to facilitate a clear understanding of the invention, the process of preparing quaternary ammonium compounds containing anhydride groups and the use thereof, the following specific embodiments are described in detail. It should be understood, however, that the detailed expositions of the instant invention, while indicating preferred embodiments, are given by way of illustration only since various changes and modifications within the spirit and scope of the invention will become apparent to those skilled in the art from this detailed description.

PRELIMINARY EXAMPLE

Screening tests for suitable cosurfactants to be used as additives for enhanced oil recovery have been developed which indicate a relationship exists between interfacial tension of the cosurfactant and petroleum removal from core samples using a micellar solution. Surfactant-stabilized dispersions of water in hydrocarbon are micellar solutions. In addition to the required surfactant, water and hydrocarbon, micellar solutions can contain cosurfactants and electrolytes to improve stability. Alcohols such as isopropanol and amyl alcohols typically have served as cosurfactants. Sodium chloride and sodium sulfate are examples of electrolytes that are used.

Important aspects of a micellar solution include an ability to solubilize water, compatibility with hydrocarbon and crude oil, an increasing viscosity with increased water concentration and inversion to an oil-in-water solution. In a micelle, surfactant and cosurfactant surround dispersed water which exists in the hydrocarbon phase as spherical droplets. With additional water, the water droplets increase in size. When water is in dispersed phase, the micellar solutions exhibit hydrocarbon-like properties of the external phase. As more and more water is solubilized in a micellar system, spheres enlarge until inversion takes place to form an oil-in-water emulsion. Cosurfactants in a miscellar solution stabilize the solution to reduce incidence of inversion and phase separation.

The following bench test has been devised as a preliminary vial screening test to eliminate need for expensive core tests of cosurfactants. The test has been found to have reliability in predicting suitable properties of cosurfactants when used in micellar solutions. The principal important aspect has been found to be the interfacial tension of the cosurfactant in an oil-water mixture. The formulation is required to yield stable fluids in brine and to show low interfacial tension (IFT) as well as very good miscibility with crude petroleum.

Micellar fluids formulated from concentrates containing 40:1 to 5:1 surfactant-cosurfactant ratios have been tested over a wide range of salinities (sodium chloride in water) and hard waters, being examined for phase stability, fluid clarity, interphase behavior and miscibility of aqueous fluids with crude petroleum.

The vial screening bench test is an empirical test which comprises mixing the micellar fluid and crude petroleum by swirling the fluids together in a test tube while observing the interface. A light source is used to observe the fluid-oil behavior. The interfacial mixing (and hence interfacial tension) is judged upon a scale of very low, moderately low, low, medium and high by a comparison with standards previously developed.

For example, brine solutions of a hardness range from under 6,000 ppm of monovalent ions (sodium chloride) to about 50,000 ppm of monovalent ions (sodium chloride) are mixed with a 40:1 ratio of surfactant-cosurfactant mixture with Second Wall Creek crude. The surfactant is a petroleum sulfonate. Surfactant-cosurfactant-brine mixtures are prepared at ambient temperature and pressure.

Stability of the brine solution with surfactant-cosurfactant mixture is tested by pouring the mixture into a 50 ml graduated cylinder and allowing the solution to stand for one hour undisturbed. Fluids which remain single phase and free of sediment are further tested. 20 ml of solutions are poured into a vial. 4 ml of crude petroleum are added to the vial. The vial is turned gently, observing mixing behavior of crude and micellar fluid. The vial is then shaken vigorously for one minute, after which the vial is allowed to stand undisturbed for one hour. After this period, the fluid is evaluated for oil drop-out, number of liquid phases, thickness of emulsion and miscibility. Results are correlated with interfacial tension of solution and crude by visual observation and spinning drop method of J. L. Caylas, et al., "Low Interfacial Tension," American Chemical Society Series No. 8 *Adsorption At Interfaces,* 1975. Formation of round oil droplets which separate quickly, and failure to form an emulsion, indicate a high, ineffective interfacial tension characteristic which can render the cosurfactant unsuitable as an additive for enhanced oil recovery applications.

EXAMPLE I

A mixture of 12.6 g (0.1 mole) of dimethylmaleic anhydride, 17.8 g (0.1 mole) of N-bromosuccinimide, 0.2 g of benzoyl peroxide, and 150 ml of carbon tetrachloride was stirred and refluxed for 26 hours. At 10 hours, we added another 0.2 g of benzoyl peroxide. The mixture was cooled to 25° C. and filtered, giving 10 g of succinimide (theory, 9.9 g). The filtrate was diluted with 50 ml of n-hexane, the lower layer separated and evaporated, giving 18.02 g (88 mole% yield) of orange, viscous oil as product. It was distilled in vacuo. All but a few drops distilled as a thick yellow oil at 103°-110° C. (0.35 mm).

Anal. Calcd. for $C_6H_5BrO_3$:C,35.1; H,2.4; Br,39.0. Found: C,34.6; H,2.5; Br,38.2.

EXAMPLE II

A solution of 12.6 g (0.1 mole) of dimethylmaleic anhydride in 38.45 ml (0.3 mole) of bromotrichloromethane was irradiated with a 275 watt G. E. sunlamp at 70°-80° C. for 19 hours. Distillation gave 5.5 ml of chloroform at 62°-80° C., 24 ml of bromotrichloromethane at 80°-90° C. (200 mm), and 15.12 g of methyl bromomethylmaleic anhydride at 102°-106° C. (0.2 mm).

Anal. Calcd. as in Example I. Found: C, 35.6; H, 2.6; Br, 38.1.

The products of both Examples I and II showed peaks for $CH_2Br$ at 4.25 ppm in the H spectrum and at 16.0 ppm in the $^{13}C$ spectrum.

EXAMPLE III

To a solution of 2.18 g (10 mmoles) of the product of Example I in 5 ml of dichloromethane was added a solution of 4.37 ml (10 mmoles) of tri-n-octylamine in 5 ml of dichloromethane. The solution became hot and turned deep purple. After two days at 25° C. the mixture was diluted with 10 ml of tert-butanol and evaporated at 80° C. to constant weight. The product,

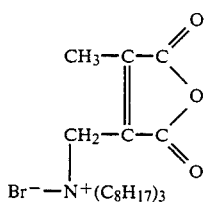

was an extremely viscous, dark oil that weighed 5.57 g (98 mole% yield).

Anal. Calcd. for $C_{30}H_{56}NBrO_3$:C, 64.5; H, 10.0; N, 2.5; Br, 14.3. Found: C, 64.8; H, 10.4; N, 2.8; Br, 14.0.

EXAMPLE IV

To a solution of 2.18 g (10 mmoles) of methyl bromomethylmaleic anhydride (Example I) in 5 ml of dichloromethane was added a solution of 2.7 g (10 mmoles) of tri-n-hexylamine in 5 ml of dichloromethane. Treatment of the dark purple solution and workup as in Example II gave 4.4 g (90 mole% yield) of extremely viscous dark oil.

Anal. Calcd. for $C_{24}H_{44}NBrO_3$,

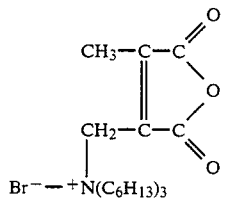

C, 60.8; H, 9.3; N, 3.0; Br, 16.9. Found: C, 61.2; H, 9.2; N, 3.4; Br, 16.2.

EXAMPLE V

A mixture of 2.18 g (10 mmoles) of methyl bromomethylmaleic anhydride and 0.791 g (10 mmoles) of pyridine, each dissolved in 5 ml of dichloromethane, was treated as in Example III. The product was a dark, hygroscopic solid, 2.9 g (100% yield).

Anal. Calcd. for $C_{11}H_{10}NBrO_3$,

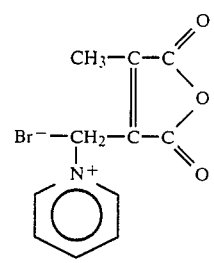

C, 46.5; H, 3.5; N, 4.9; Br, 28.2. Found: C, 46.1; H, 3.9; N, 5.4; Br, 27.8.

EXAMPLE VI

The effectiveness of these novel compounds as surfactants in lowering interfacial tension between solvent-extracted 5W oil and water was measured using a Cenco-Du Nouy Interfacial Tensiometer No. 70545 with a 6 cm platinum-iridium ring at 25° C., with double-distilled water, with these results at 1 wt% concentrations.

| Product | Interfacial Tension, dynes/cm |
|---|---|
| Control | 41.73 |
| Example III | 11.23 |
| Example IV | 13.66 |
| Example V | 19.80 |

EXAMPLE VII

Control of microorganisms in inhibiting or preventing growth of fungi in enhanced oil recovery operations is a desirable characteristic of useful additives.

The product of this invention was tested as a biocide and inhibitor for the growth of microorganisms by this test: 25 g of agar preparation were placed in standard petri dishes. The agar preparation consisted of 23.5 g of Bacto Plate Count Agar, Difco Laboratories, Detroit, Mich., dissolved in 1 liter of water. Plate Count Agar contains a standard USP formula for nutrient agar, consisting of:

5 g: Pancreatic digest of casein
2.5 g: Yeast extract
1 g: Glucose
15 g: Agar

Four petri dishes were untreated and used as blanks. To the others, in duplicate, were added 2.5 ml of 1% acetone solutions of the products of Examples I, III, IV, and V. All plates were uncovered for 4 hours to expose them to the spores of adventitious fungi and bacteria, then covered and stored at 30° C. for 6 days. Ratings were given at this point; 0 represents no growth, 5 shows luxuriant colonies of fungi and bacteria. Results were as follows:

| Product of Example No. | Growth |
|---|---|
| Control | 5,5 |
| Example I | 0,0 |
| Example III | 0,0 |

| Product of Example No. | Growth |
|---|---|
| Example IV | 0,0 |
| Example V | 3,0 |

EXAMPLE VIII

The compounds of Examples III, IV and V were tested in the vial test as cosurfactants for enhanced oil recovery, using 5% petroleum sulfonate as surfactant in brine (NaCl), adding the cosurfactant to surfactant and noting the stability of the mixture, as brine tends to cause the surfactant to separate (salt) out. The brine-surfactant-cosurfactant mixture is then mixed by shaking with crude petroleum and the interfacial tension (IFT) observed. Low IFT is indicated by easy mixing of the two phases with no separation. Formation of round oil droplets that separate quickly indicates a high, ineffective IFT.

The vial test consisted of adding 0.1 g of cosurfactant to 20 ml of stock solution (5 wt% of crude oil sulfonate, A-152 or V-60 sulfonate, in 0.1N aqueous sodium chloride), adding 2 ml of crude oil, and shaking vial vigorously. A good vial test (+) results in an emulsion stable for 2 hours at 25° C.

Products of Examples III and IV proved effective in lowering the IFT in the vial test, giving mixtures of brine-surfactant-cosurfactant fluids which were stable, did not separate, and easily formed mixtures of the fluid with crude petroleum. Product of Example V was ineffective. These novel compounds can be used in solutions at 0.01 to 10% by weight.

EXAMPLE IX

A micellar slug for micellar flooding consisting of 3 (vol)% petroleum sulfonate as surfactant, 2 (vol)% petroleum hydrocarbon, 1 (vol)% cosurfactant comprising a quaternary ammonium compound containing anhydride groups prepared from methyl bromomethylmaleic anhydride and tri-n-hexylamine in a 1.0N NaCl brine solution is prepared. The micellar slug fluid is fed into the high pressure injection pump and is injected into a 25 foot section sandstone formation in Crawford County, Ill., USA, through an injection well at 900 psig. The amount of slug injected is about 7% of reservoir pore volume and the petroleum hydrocarbon is lease crude oil. Pattern of injection is two rows of injection wells and three rows of producer wells. There are nine wells in each row and total area enclosed is 40 acres. Injection and production wells are 460 feet apart and adjacent wells are 115 feet apart. Crude oil production increases to recover about 30% of the oil in place at start of the injection.

What is claimed is:

1. A composition of the structural formula:

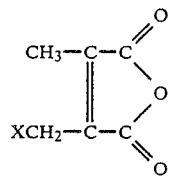

wherein X is halogen.

2. The composition of claim 1 wherein said composition is methyl bromomethylmaleic anhydride.

3. A method of preparing methyl bromomethylmaleic anhydride of the structural formula

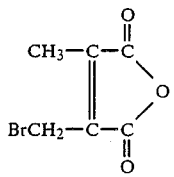

wherein said anhydride is prepared by reacting dimethylmaleic anhydride with bromotrichloromethane in the presence of actinic radiation, and recovering said anhydride by distilling at a temperature of from about 100° to about 106° C. and from about 0.2 to about 0.3 mm Hg.

* * * * *